United States Patent
Yu et al.

(10) Patent No.: US 9,545,214 B2
(45) Date of Patent: Jan. 17, 2017

(54) HEART RATE METER AND METHOD THEREOF

(71) Applicant: Quanta Computer Inc., Kuei Shan Hsiang, Tao Yuan Shien (TW)

(72) Inventors: Chih-Hsiung Yu, Tao Yuan Shien (TW); Yung-Ming Chung, Tao Yuan Shien (TW); Yen-Chih Huang, Tao Yuan Shien (TW)

(73) Assignee: QUANTA COMPUTER INC., Guishan Dist., Taoyuan (TW)

( * ) Notice: Subject to any disclaimer, the term of this patent is extended or adjusted under 35 U.S.C. 154(b) by 63 days.

(21) Appl. No.: 14/458,562

(22) Filed: Aug. 13, 2014

(65) Prior Publication Data

US 2015/0359451 A1     Dec. 17, 2015

(30) Foreign Application Priority Data

Jun. 11, 2014   (TW) .............................. 103120133 A

(51) Int. Cl.
*A61B 5/04*     (2006.01)
*A61B 5/0432*   (2006.01)
*A61B 5/00*     (2006.01)

(52) U.S. Cl.
CPC ............ *A61B 5/0432* (2013.01); *A61B 5/681* (2013.01); *A61B 5/6844* (2013.01); *A61B 5/7203* (2013.01); *A61B 2560/0209* (2013.01)

(58) Field of Classification Search
None
See application file for complete search history.

(56) References Cited

U.S. PATENT DOCUMENTS

| | | | | |
|---|---|---|---|---|
| 5,738,104 A | * | 4/1998 | Lo ..................... | A61B 5/02438 600/509 |
| 7,285,090 B2 | * | 10/2007 | Stivoric ................. | A61B 5/01 128/905 |
| 2012/0081106 A1 | * | 4/2012 | Grinberg ............... | G01B 7/023 324/207.15 |
| 2012/0101690 A1 | * | 4/2012 | Srinivasan ........... | A61B 5/0408 701/45 |
| 2014/0107493 A1 | * | 4/2014 | Yuen .................... | H04W 4/027 600/473 |
| 2014/0125491 A1 | * | 5/2014 | Park ..................... | H04W 4/027 340/870.01 |
| 2014/0125618 A1 | * | 5/2014 | Panther ................ | A61B 5/6838 345/173 |
| 2014/0125619 A1 | * | 5/2014 | Panther ............... | G06F 3/04883 345/173 |

(Continued)

*Primary Examiner* — Brian T Gedeon
*Assistant Examiner* — Ankit D Tejani
(74) *Attorney, Agent, or Firm* — McClure, Qualey & Rodack, LLP

(57) ABSTRACT

A heart rate meter and a method thereof are provided. The method is adopted by a sensing circuit of a heart rate meter, wherein the sensing circuit includes a pulse sensor and a proximity sensor. The method includes: determining whether the sensing circuit is close to a neighboring object according to a proximity output signal of the proximity sensor; determining whether the sensing circuit is hung in the air according to a direct current (DC) output signal of the pulse sensor; and when the sensing circuit is close to the neighboring object and is not hung in the air, determining that the measuring circuit can measure an electrocardiographic signal of the neighboring object.

6 Claims, 7 Drawing Sheets

(56) References Cited

U.S. PATENT DOCUMENTS

| | | | |
|---|---|---|---|
| 2014/0125620 A1* | 5/2014 | Panther | G06F 3/011 345/173 |
| 2014/0127996 A1* | 5/2014 | Park | H04W 4/027 455/41.1 |
| 2014/0135612 A1* | 5/2014 | Yuen | A61B 5/02405 600/407 |
| 2014/0135631 A1* | 5/2014 | Brumback | A61B 5/02438 600/479 |
| 2014/0142403 A1* | 5/2014 | Brumback | A61B 5/02433 600/324 |

\* cited by examiner

HEART RATE METER AND METHOD THEREOF

CROSS REFERENCE TO RELATED APPLICATIONS

This Application claims priority of Taiwan Patent Application No. 103120133, filed on Jun. 11, 2014, the entirety of which is incorporated by reference herein.

BACKGROUND OF THE INVENTION

Field of the Invention

The present invention relates to medical equipment, and in particular to a heart rate meter and a method thereof.

Description of the Related Art

As an increasing number of people suffer any form of cardiovascular diseases, the market for heart rate meters increases accordingly.

Typically, conventional heart rate meters employ green light lasers and optical sensors to measure pulses on a patient's wrist. This type of pulse sensor integrates a green light laser and an optical sensor into a single package, consequently it cannot identify whether the pulse sensor has already been positioned on the wrist so that it can start sensing the pulses correctly.

Therefore, a heart rate meter and a sensing method are required to accurately identify when a pulse sensor has been placed on a wrist, effectively eliminating noises in calculating pulses and a heart rate and reducing power consumption in the system.

BRIEF SUMMARY OF THE INVENTION

A detailed description is given in the following embodiments with reference to the accompanying drawings.

An embodiment of a method is disclosed, adopted by a sensing circuit of a heart rate meter, wherein the sensing circuit comprises a pulse sensor and a proximity sensor. The method includes: determining whether the sensing circuit is close to a neighboring object according to a proximity output signal of the proximity sensor; determining whether the sensing circuit is not in direct contact to the neighboring object according to a direct current (DC) output signal of the pulse sensor; and when the sensing circuit is close to the neighboring object and is in direct contact to the neighboring object, determining that the measuring circuit can measure an electrocardiographic signal of the neighboring object.

An embodiment of a heart rate meter is disclosed, including a sensing circuit and a controller. The sensing circuit includes a proximity sensor and a pulse sensor. The proximity sensor is configured to determine a proximity output signal representing whether the sensing circuit is close to a neighboring object. The pulse sensor is configured to determine a direct current (DC) output signal representing whether the sensing circuit is not in direct contact to the neighboring object. The controller is configured to determine whether the sensing circuit is close to a neighboring object according to the proximity output signal, determine whether the sensing circuit is not in direct contact to the neighboring object according to the DC output signal, and when the sensing circuit is close to the neighboring object and is in direct contact to the neighboring object, determine that the measuring circuit can measure an electrocardiographic signal of the neighboring object.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
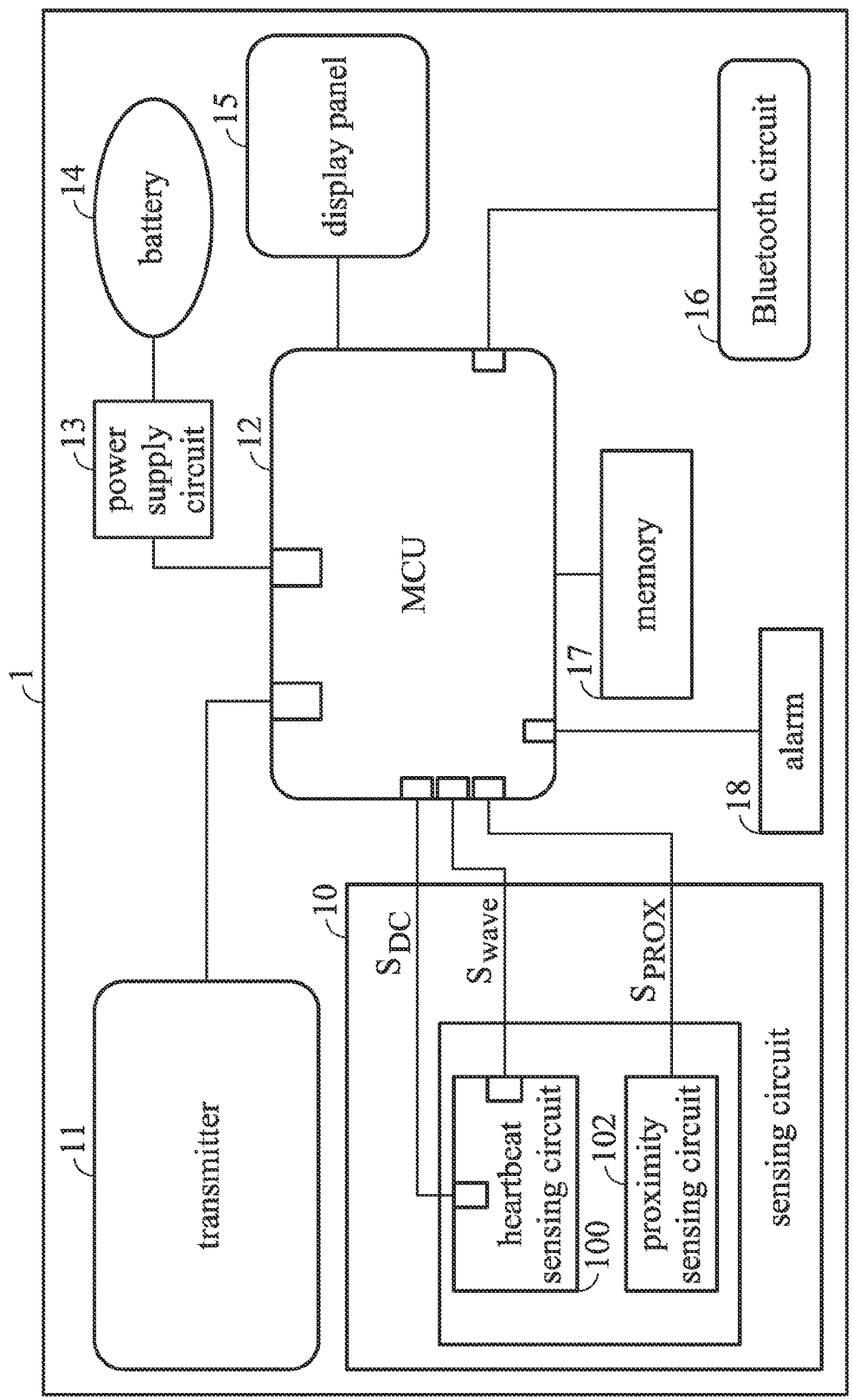
FIG. 1 is a block diagram of a heart rate (heartbeat) meter 1 according to an embodiment of the invention.

FIG. 1 is a block diagram of a heart rate (heartbeat) meter 1 according to an embodiment of the invention, including a sensing circuit 2, a signal transmitter 11, a microcontroller unit (MCU) 12 (controller), a power supply circuit 13, a battery 14, a display panel 15, a Bluetooth circuit 16, a memory 17, and an alarm 18. The heart rate meter 1 is a piece of medical electronic equipment which automatically records a bioelectrical signal (electrocardiographic signal) generated by a cardiac muscle during heart actions, often employed in clinic trials and scientific studies.

The sensing circuit 2 is configured to sense the bioelectrical signal generated in the heart actions of an end-user, containing a heartbeat sensing circuit 100 (pulse sensor) and a proximity sensing circuit 102 (proximity sensor). When the heart rate meter 1 measures an electrocardiographic signal $S_{wave}$, the sensing circuit 2 will be stuck, tied, or otherwise fixed to an object under test such as a wrist or a body part on which the electrocardiographic signal may be detected. The electrocardiographic signal $S_{wave}$ includes a heartbeat or a pulse signal. The heartbeat sensing circuit 100 and proximity sensing circuit 102 on the sensing circuit 2 are configured to sense the location of the object under test, to prevent it from measuring an incorrect electrocardiographic signal $S_{wave}$. The proximity sensing circuit 102 is configured to sense whether a neighboring object such as a wrist is present beyond a predetermined range, and output a proximity output signal $S_{PROX}$ which represents whether the sensing circuit 2 is close to the neighboring object. For example, the proximity sensing circuit 102 can detect a neighboring object beyond a range of 1 cm; and cannot detect the proximity sensing circuit 102 within the range of 1 cm, thus it relies on the heartbeat sensing circuit 100 to determine whether the sensing circuit 2 is not in direct contact to the neighboring object or fixed to the object under test. As a result, the heartbeat sensing circuit 100 is configured to sense whether the sensing circuit 2 is hung in the air not in direct contact to the neighboring object and output a direct current (DC) output signal $S_{DC}$ which represents whether the sensing circuit 2 is not in direct contact to the neighboring object. For example, when the sensing circuit 2 is fixed to an object under test, the heartbeat sensing circuit 100 will generate a DC output signal $S_{DC}$ that is less than a predetermined voltage, such as 2.9V. The heartbeat sensing circuit 100 may also output a sensed electrocardiographic signal $S_{wave}$.

The MCU 12 receives the proximity output signal $S_{PROX}$ from the proximity sensing circuit 102 and determines whether the sensing circuit 2 is close to the neighboring object based on the proximity output signal $S_{PROX}$. In addition, the MCU 12 further receives the DC output signal $S_{DC}$ from the heartbeat sensing circuit 100 and determines whether the sensing circuit 2 is close to the neighboring object based on the DC output signal $S_{DC}$. Only when the sensing circuit 2 is close to the neighboring object and is in direct contact to the neighboring object, the MCU 12 can determine that the sensing circuit 2 can measure an electrocardiographic signal $S_{wave}$ of the neighboring object, i.e., the electrocardiographic signal $S_{wave}$ measured by the heartbeat sensing circuit 100 is valid. When the sensing circuit 2 is beyond the predetermined range, the MCU 12 determines that the sensing circuit 2 is not fixed to the neighboring object, and thus the electrocardiographic signal $S_{wave}$ measured by the heartbeat sensing circuit 100 is invalid. When the sensing circuit 2 is close to the object under test and is not in direct contact to the neighboring object, the MCU 12 determines that the sensing circuit 2 is close to the neighboring object but not in direct contact, and thus the electrocardiographic signal $S_{wave}$ measured by the heartbeat sensing circuit 100 is invalid.

The MCU 12 can communicate with the heartbeat sensing circuit 100 and proximity sensing circuit 102 by means of wired or wireless connections. For example, the MCU 12 may communicate with the heartbeat sensing circuit 100 and proximity sensing circuit 102 by the I2C wired communication protocol. In another example, the MCU 12 may communicate with the heartbeat sensing circuit 100 and proximity sensing circuit 102 by the Bluetooth wireless communication protocol. Moreover, the MCU 12 and the sensing circuit 2 may be disposed on the same or different devices.

The signal transmitter 11 is configured to transmit a light signal such as a green beam laser to a neighboring object or a body part. During heart contractions and relaxations, blood will carry different concentrations of red blood cells, the red blood cells will absorb a part of the transmitted light signal and reflect another part of the transmitted light signal to the heartbeat sensing circuit 100. As a result, the heartbeat sensing circuit 100 can determine the electrocardiographic signal $S_{wave}$ by sensing the reflected light signal. The power supply circuit 13 and battery 14 are configured to provide the power supply to all circuits in the heart rate meter 1. The display panel 15 is configured to display the measured electrocardiographic signal $S_{wave}$. The Bluetooth circuit 16 is configured to perform Bluetooth communications. The memory 17 is configured to record the electrocardiographic signal $S_{wave}$ and store an application for measuring the electrocardiographic signal, wherein the application may be loaded into the MCU 12 to determine when to measure the electrocardiographic signal $S_{wave}$ of a body part, process the measured electrocardiographic signal $S_{wave}$, and determine an emergency condition based on the measured electrocardiographic signal $S_{wave}$. For example, when the magnitude of the measured electrocardiographic signal $S_{wave}$ is less than a predetermined magnitude, the application may determine that an emergency has occurred. The application may implement a sensing method 4 shown in FIG. 4. The alarm 18 is configured to generate an alert sound in an emergency.

The heart rate meter 1 in FIG. 1 adopts the heartbeat sensing circuit 100 and the proximity sensing circuit 102 to sense the location of an object under test, to prevent the measurement of an invalid electrocardiographic signal $S_{wave}$, eliminate noises from a valid electrocardiographic signal $S_{wave}$ effectively, and reduce power consumption in the system of the heart rate meter 1.

Figure 2:
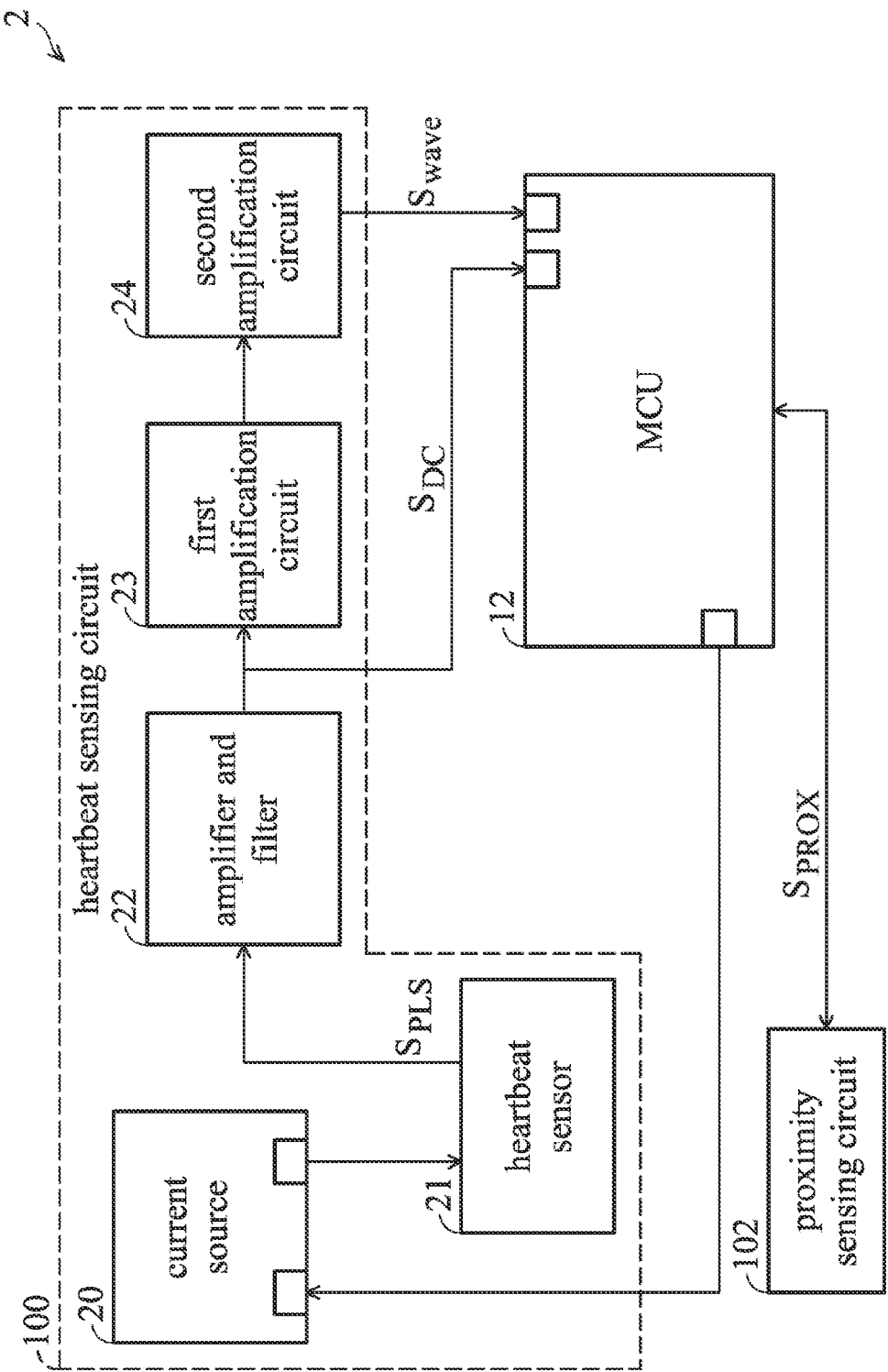
FIG. 2 is a block diagram of a sensing circuit 2 according to an embodiment of the invention.

FIG. 2 is a block diagram of a sensing circuit 2 according to an embodiment of the invention, including a heartbeat sensing circuit 100, a proximity sensing circuit 102 and an MCU 12.

The sensing circuit 2 adopts the proximity sensing circuit 102 to sense whether a neighboring object is beyond a predetermined range, the heartbeat sensing circuit 100 to sense whether the sensing circuit is not in direct contact to the neighboring object, and the MCU 12 to determine whether the sensing circuit may measure an electrocardiographic signal of the neighboring object. The proximity sensing circuit 102 can output a proximity output signal $S_{PROX}$ representing whether the sensing circuit 2 is close to the neighboring object. Because the proximity sensing circuit 102 can only detect a neighboring object beyond a predetermined range, after the proximity output signal $S_{PROX}$ indicates that no neighboring object is present beyond the predetermined range, the heartbeat sensing circuit 100 may subsequently sense whether a neighboring object is present within the predetermined range. The heartbeat sensing circuit 100 can output a DC output signal $S_{DC}$ representing whether the sensing circuit 2 is not in direct contact to the neighboring object or in direct contact with a neighboring object. When the sensing circuit 2 is in direct contact with a neighboring object, the heartbeat sensing circuit 100 can sense a stable DC voltage that is less than a predetermined voltage, e.g., 2.9V, with the stable DC voltage being the DC output signal $S_{DC}$. When the sensing circuit 2 is hung above in the predetermined range but not in direct contact with a neighboring object, the heartbeat sensing circuit 100 will sense a DC output signal $S_{DC}$ that exceeds the predetermined voltage, and the MCU 12 will determine whether a neighboring object is present in close proximity, and determine the location of the neighboring object based on the proximity output signal $S_{PROX}$ and DC output signal $S_{DC}$. The MCU 12 will then determine whether the sensing circuit 2 may measure an electrocardiographic signal of the neighboring object based on the information thereof. Specifically, only when the MCU 12 determines that a neighboring object is close to the sensing circuit 2 and that the sensing circuit 2 is in direct contact to the neighboring object based on the proximity output signal $S_{PROX}$ and DC output signal $S_{DC}$, an electrocardiographic signal $S_{wave}$ of the neighboring object then can be measured.

The heartbeat sensing circuit 100 includes a current source 20, a heartbeat sensor 21, an amplifier and filter 22, a first amplification circuit 23, and a second amplification circuit 24. The current source 20 provides a current to the heartbeat sensor 21 to sense a reflected light signal for producing a pulse signal $S_{PLS}$, which is subsequently amplified and noise-filtered by the amplifier and filter 22 to generate the DC output signal $S_{DC}$. The first amplification circuit 23 and second amplification circuit 24 then eliminate a DC component from the DC output signal $S_{DC}$, and keep an alternating current (AC) component of the DC output signal $S_{DC}$ to generate the electrocardiographic signal $S_{wave}$.

Figure 3:
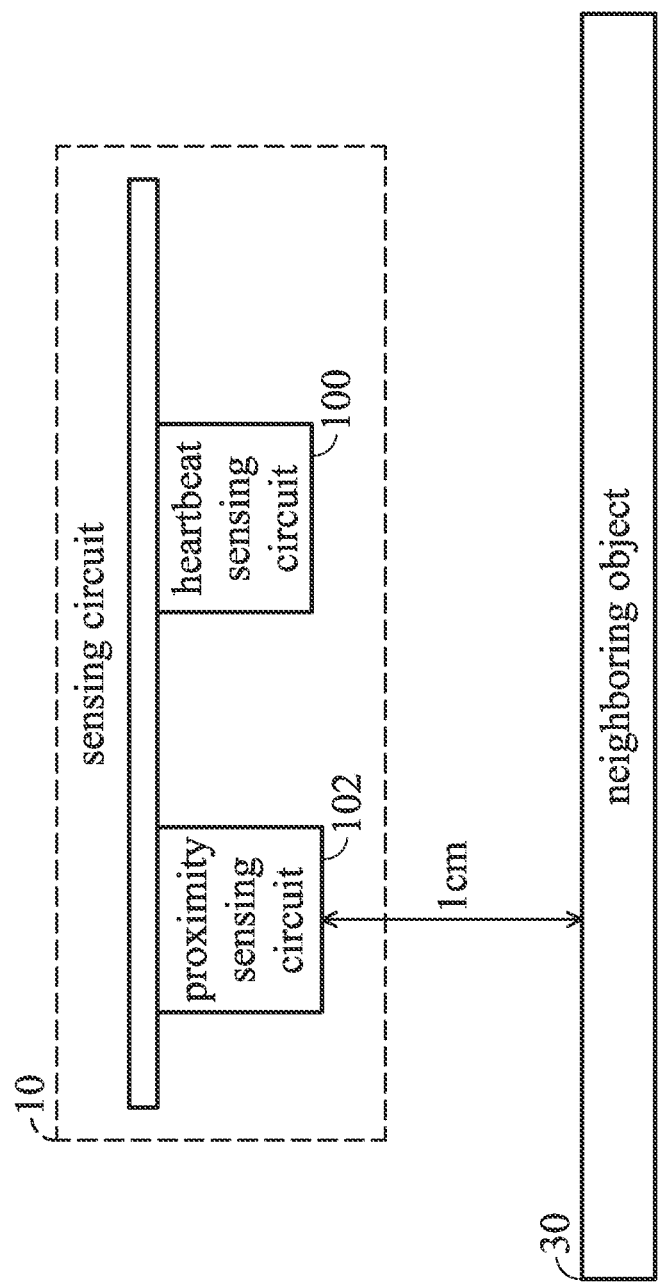
FIG. 3 is a schematic diagram illustrating how the sensing circuit 10 senses a neighboring object according to an embodiment of the invention.

FIG. 3 is a schematic diagram illustrating that the sensing circuit 10 senses a neighboring object according to an embodiment of the invention. The heartbeat sensing circuit 100 and the proximity sensing circuit 102 are disposed on the same side and adjacent to each other for sensing a neighboring object 30.

Figure 5A:
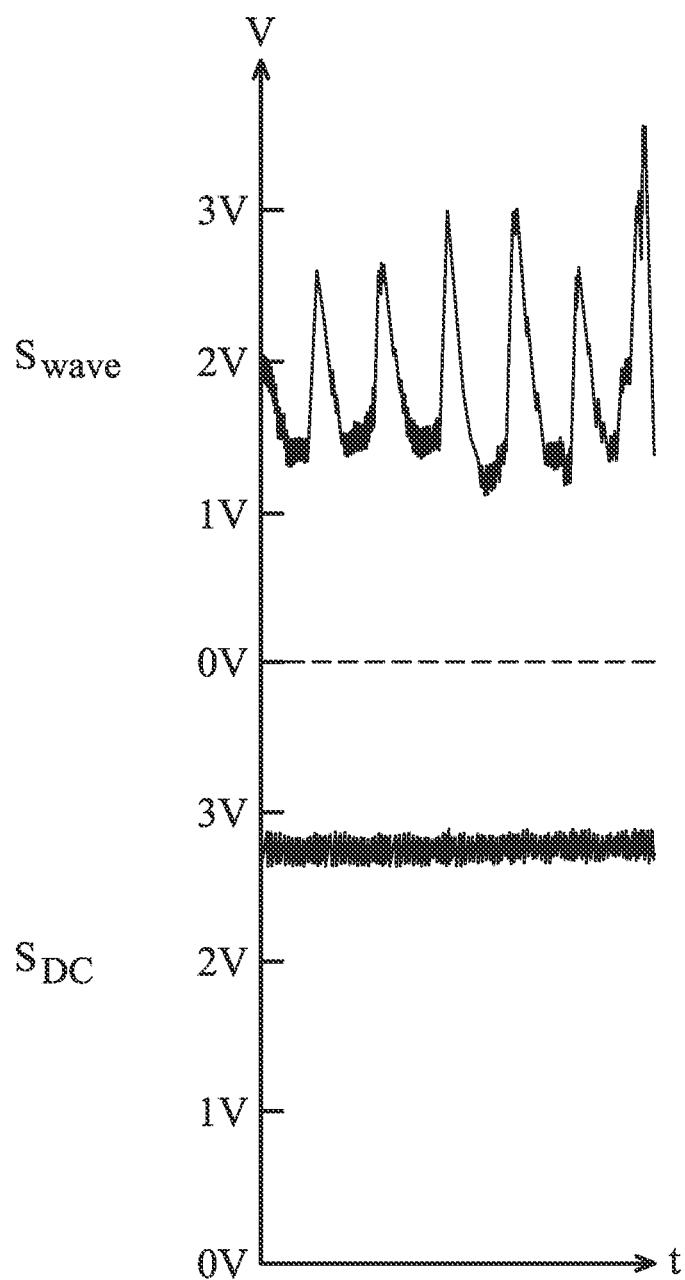
FIGS. 5A through 5C show signals output from a sensing circuit of a heart rate meter according to embodiments of the invention.
Figure 5B:
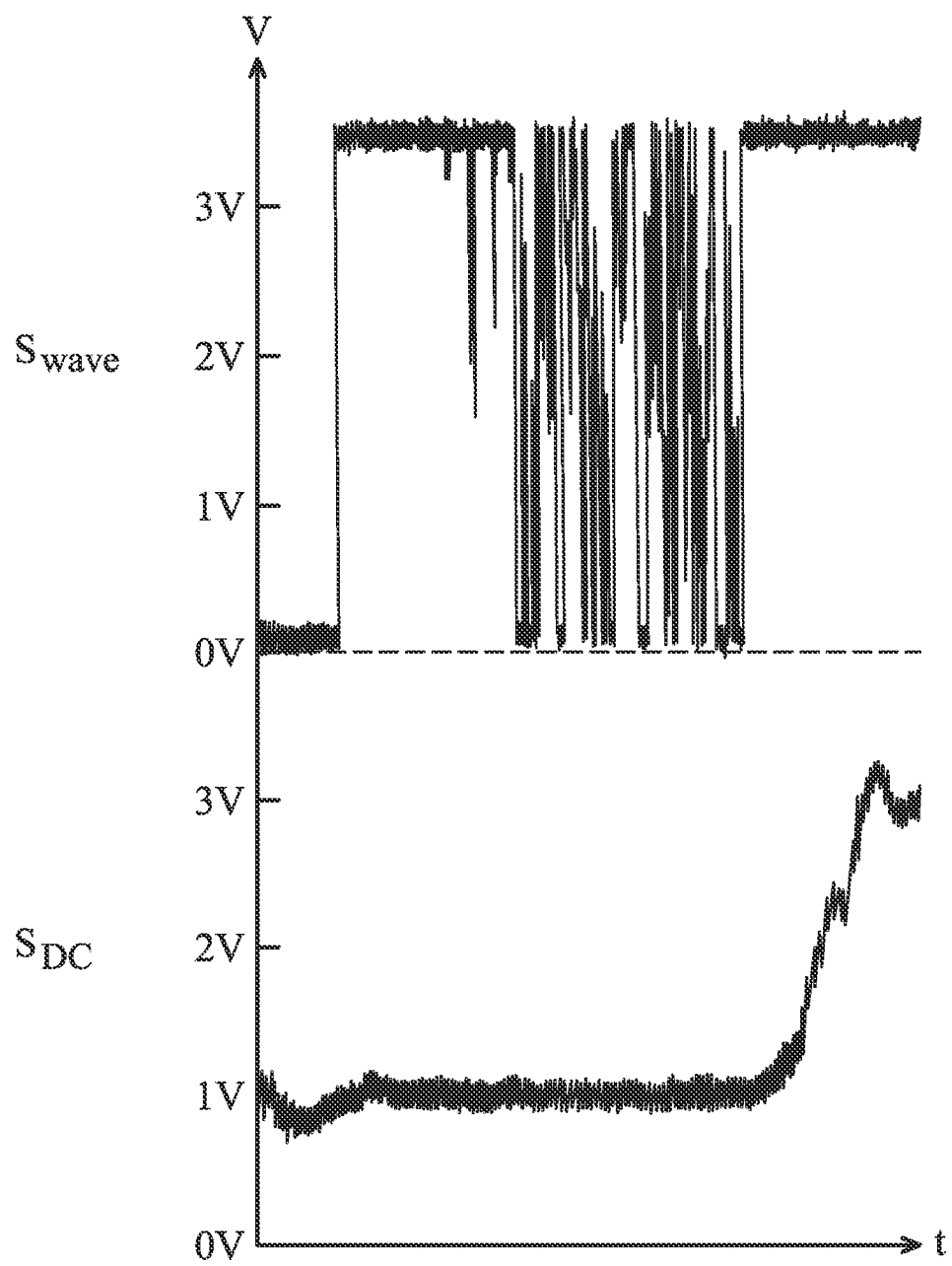

When the sensing circuit 10 is near the neighboring object 30, the heartbeat sensing circuit 100 or the proximity sensing circuit 102 will detect the presence of the neighboring object 30. When the distance between the sensing circuit 10 and the neighboring object 30 exceeds a predetermined range, e.g., 1 cm, the proximity sensing circuit 102 will sense the neighboring object 30, and the heartbeat sensing circuit 100 will sense an unstable and erratic DC output signal $S_{DC}$. Please refer to FIG. 5B: when the distance between the sensing circuit 10 and the neighboring object 30 exceeds the predetermined range, the heartbeat sensing circuit 100 will sense a constantly changing ambient light, and consequently output a DC output signal $S_{DC}$ ranging from 1V to 3V, wherein the corresponding electrocardiographic signal $S_{wave}$ shows an unstable and erratic behavior.

Figure 5C:
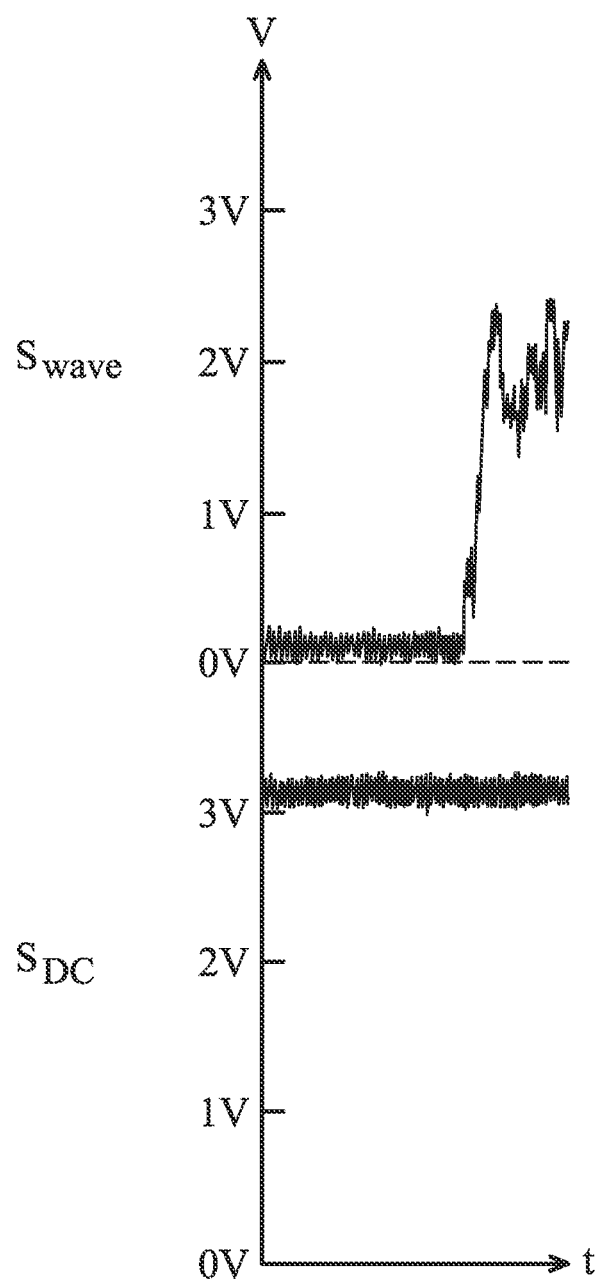

In FIG. 3, when the distance between the sensing circuit 10 and the neighboring object 30 is less than the predetermined range and the two are not in direct contact, the proximity sensing circuit 102 will not detect the presence of the neighboring object 30, the heartbeat sensing circuit 100 will detect the neighboring object 30 and produce a DC output signal SDC which exceeds a predetermined voltage, e.g., 3V. Please refer to FIG. 5C: when the distance between the sensing circuit 10 and the neighboring object 30 is less than the predetermined range and not in direct contact, the heartbeat sensing circuit 100 will sense a small and stable ambient light, and consequently output a DC output signal SDC exceeding 3V, and the corresponding electrocardiographic signal Swave shows an unstable and erratic behavior.

In FIG. 3, when the distance between the sensing circuit 10 and the neighboring object 30 is in direct contact, the heartbeat sensing circuit 100 will generate a DC output signal SDC which is less than a predetermined voltage, e.g., 3V. Please refer to FIG. 5A, when the sensing circuit 10 and the neighboring object 30 are in direct contact, the heartbeat sensing circuit 100 will sense a light signal reflected by the neighboring object 30. The reflected light signal is typically less than the ambient light, and consequently the heartbeat sensing circuit 100 will output a DC output signal SDC less than 3V. When the neighboring object 30 is a human body part, the heartbeat sensing circuit 100 will generate a regular electrocardiographic signal Swave based on the DC output signal SDC.

Figure 4:
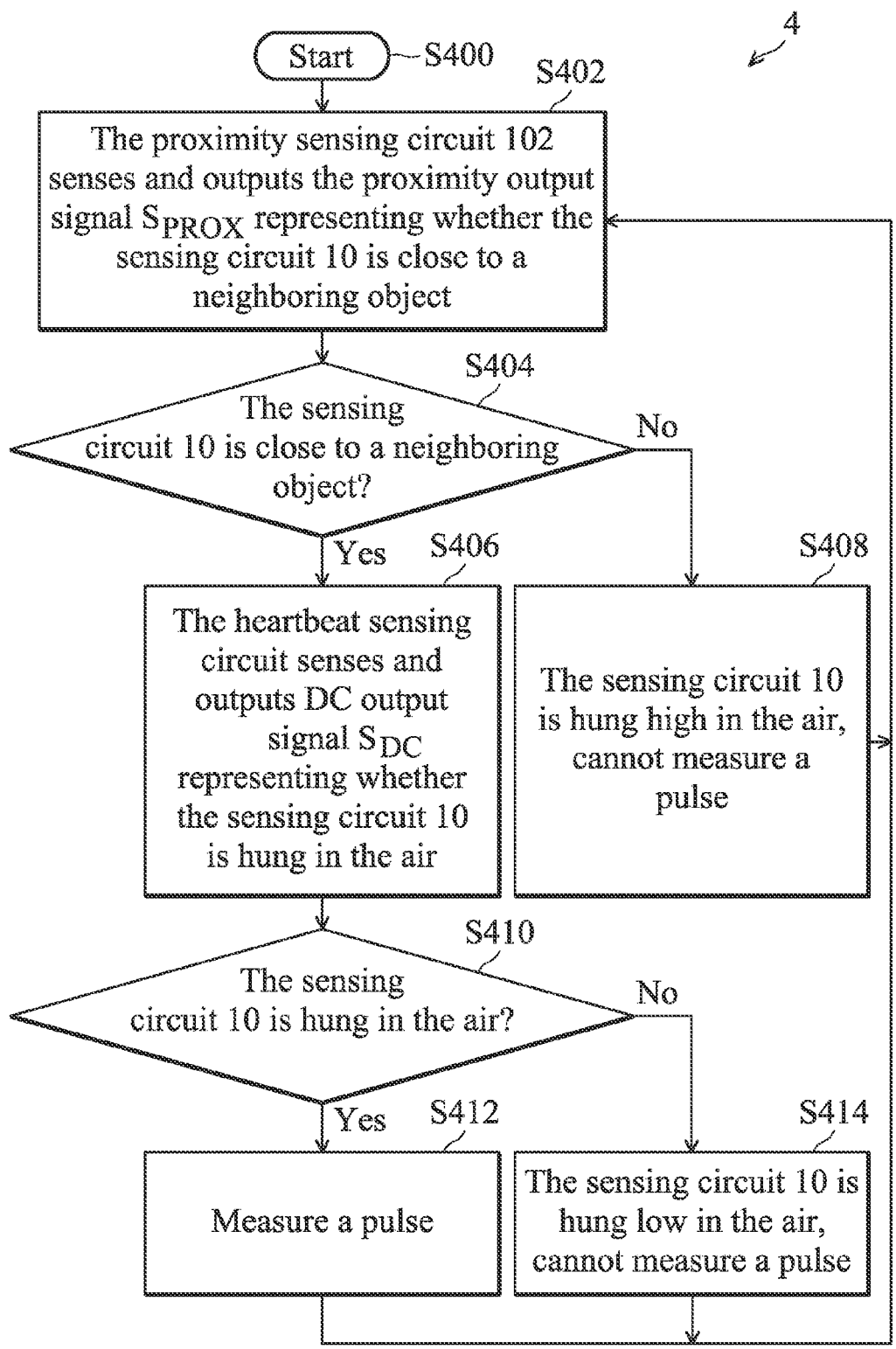
FIG. 4 is a flowchart of a sensing method 4 according to an embodiment of the invention.

FIG. 4 is a flowchart of a sensing method 4 according to an embodiment of the invention, incorporating the heart rate meter 1 in FIG. 1. The sensing method 4 may be implemented by program code stored in the memory 17.

When the heart rate meter 1 is powered on, the MCU 12 is configured to load program code from the memory 17 to determine the distance between the sensing circuit 10 and the neighboring object and whether an electrocardiographic signal $S_{wave}$ should be measured (S400). Initially, the proximity sensing circuit 102 continues sensing and outputs a proximity output signal $S_{PROX}$ representing whether the sensing circuit 10 is close to the neighboring object to the MCU 12 (S402). Subsequently, the MCU 12 determines whether the sensing circuit 10 is close to any neighboring object based on the proximity output signal $S_{PROX}$ (S404). If the sensed neighboring object is present beyond the predetermined range, the MCU 12 determines that the sensing circuit 10 is placed beyond a predetermined range and is not close to any neighboring object, thus no pulse or other electrocardiographic signals are measured (S408). If the sensed neighboring object is present within the predetermined range (S406), the MCU 12 then receives a DC output signal $S_{DC}$ from the heartbeat sensing circuit 100 to determine whether the sensing circuit 10 is not in direct contact to the neighboring object (S410). When the DC output signal $S_{DC}$ exceeds a predetermined voltage, it indicates that the sensing circuit 10 is not in direct contact to the neighboring object; whereas when the DC output signal $S_{DC}$ is less than the predetermined voltage, it indicates that the sensing circuit 10 is in direct contact with a neighboring object. As a result, when determining that the DC output signal $S_{DC}$ exceeds the predetermined voltage, the MCU 12 will determine that the sensing circuit 10 is placed within a predetermined range and is not in direct contact with the neighboring object, and thus no pulse or other electrocardiographic signals are measured (S414). In contrast, when determining that the DC output signal $S_{DC}$ is less than the predetermined voltage, the MCU 12 will determine that the sensing circuit is in direct contact with the neighboring object, and pulses or other electrocardiographic signals should be measured (S412). After the sensing method 4 has determined whether an electrocardiographic signal of a neighboring object should be measured in Steps S408, S412, and S414, it can return to Step S402 to restart the sensing method 4 to determine whether there is an electrocardiographic signal of another neighboring object to be measured.

The sensing method 4 in FIG. 4 adopts the heartbeat sensing circuit 100 and the proximity sensing circuit 102 to sense the location of an object under test, to prevent the measurement of an invalid electrocardiographic signal $S_{wave}$, eliminate noises from a valid electrocardiographic signal $S_{wave}$ effectively, and reduce power consumption in the system of the heart rate meter 1.

As used herein, the term "determining" encompasses calculating, computing, processing, deriving, investigating, looking up (e.g., looking up in a table, a database or another data structure), ascertaining and the like. Also, "determining" may include resolving, selecting, choosing, establishing and the like.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device, discrete gate or transistor logic, discrete hardware components or any combination thereof designed to perform the functions described herein. A general purpose processor may be a microprocessor, but in the alternative, the processor may be any commercially available processor, microprocessor or state machine.

The operations and functions of the various logical blocks, modules, and circuits described herein may be implemented in circuit hardware or embedded software codes that can be accessed and executed by a processor.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method, adopted by a sensing circuit of a heart rate meter, wherein the sensing circuit comprises a pulse sensor and a proximity sensor, the method comprising:
when a proximity output signal of the proximity sensor indicates that a predetermined distance is not exceeded, determining the sensing circuit is close to a neighboring object;
when a direct current (DC) output signal of the pulse sensor is less than a predetermined voltage, determining that the sensing circuit is direct contact to the neighboring object;
when the sensing circuit is close to the neighboring object and is in direct contact to the neighboring object, determining that an electrocardiographic signal of the neighboring object measured by the pulse sensor is valid;
when the electrocardiographic signal of the neighboring object measured by the pulse sensor is valid, recording the electrocardiographic signal, displaying the measured electrocardiographic signal, and/or determining whether an emergency has occurred based on the measured electrocardiographic signal
when the sensing circuit is close to the neighboring object but not in direct contact with the neighboring object, the electrocardiographic signal measured by the pulse sensor is invalid; and
when the sensing circuit is beyond the predetermined distance, detecting the neighboring object by the proximity sensor.

2. The method of claim 1, wherein the pulse sensor and the proximity sensor are disposed alongside one another on a sensing circuit.

3. The method of claim 1, further comprising:
generating an alert sound when the emergency has occurred.

4. A heart rate meter, comprising:
a sensing circuit, comprising:
a proximity sensor, configured to determine a proximity output signal when the sensing circuit is beyond a predetermined distance;
a pulse sensor, configured to determine that the sensing circuit is direct contact to a neighboring object when a direct current (DC) output signal of the pulse sensor is less than a predetermined voltage;
a controller, configured to determine that, when the proximity output signal of the proximity sensor indicates that the predetermined distance is not exceeded, the sensing circuit is close to the neighboring object, and when the sensing circuit is close to the neighboring object but not in direct contact with the neighboring object, determine that the electrocardiographic signal measured by the pulse sensor is invalid, and when the sensing circuit is close to the neighboring object and is in direct contact to the neighboring object, determine that an electrocardiographic signal of the neighboring object measured by the pulse sensor is valid, and when the electrocardiographic signal of the neighboring object measured by the pulse sensor is valid, record the electrocardiographic signal, and determine whether an emergency has occurred based on the measured electrocardiographic signal; and
a display panel, configured to display the measured electrocardiographic signal when the electrocardiographic signal of the neighboring object measured by the pulse sensor is valid.

5. The heart rate meter of claim 4, wherein the pulse sensor and the proximity sensor are disposed alongside one another on a sensing circuit.

6. The heart rate meter of claim 4, wherein an alarm device generates an alert sound when the emergency has occurred.

* * * * *